(12) United States Patent
Budd et al.

(10) Patent No.: US 9,169,215 B2
(45) Date of Patent: Oct. 27, 2015

(54) LPAR—SUBSTITUTED CYANOPYRAZOLE COMPOUNDS

(71) Applicant: Hoffmann-La Roche Inc., Nutley, NJ (US)

(72) Inventors: David Budd, Wayne, NJ (US); Yimin Qian, Plainsboro, NJ (US); Ryan Craig Schoenfeld, Basking Ridge, NJ (US); Achyutharao Sidduri, West Orange, NJ (US)

(73) Assignee: HOFFMANN-LA ROCHE INC., Nutley, NJ (US)

( * ) Notice: Subject to any disclaimer, the term of this patent is extended or adjusted under 35 U.S.C. 154(b) by 0 days.

(21) Appl. No.: 14/421,094

(22) PCT Filed: Sep. 2, 2013

(86) PCT No.: PCT/EP2013/068083
§ 371 (c)(1),
(2) Date: Feb. 11, 2015

(87) PCT Pub. No.: WO2014/037303
PCT Pub. Date: Mar. 13, 2014

(65) Prior Publication Data
US 2015/0218106 A1 Aug. 6, 2015

Related U.S. Application Data

(60) Provisional application No. 61/696,862, filed on Sep. 5, 2012.

(51) Int. Cl.
C07D 231/38 (2006.01)

(52) U.S. Cl.
CPC .................................. *C07D 231/38* (2013.01)

(58) Field of Classification Search
CPC ...................................................... C07D 231/38
See application file for complete search history.

(56) References Cited

FOREIGN PATENT DOCUMENTS

WO    WO 02/23986    *  3/2002    ............ 514/407

* cited by examiner

*Primary Examiner* — Samantha Shterengarts

(57) ABSTRACT

Provided herein are compounds of the formula (I), as well as pharmaceutically acceptable salts thereof, wherein the substituents are as those disclosed in the specification. These compounds, and the pharmaceutical compositions containing them, are useful for the treatment of inflammatory diseases and disorders such pulmonary fibrosis.

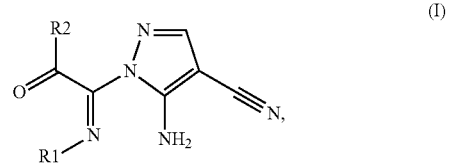

(I)

12 Claims, No Drawings

LPAR—SUBSTITUTED CYANOPYRAZOLE COMPOUNDS

This application is a National Stage Application of PCT/EP2013/068083 filed Sep. 2, 2013, which claims priority from U.S. Provisional Patent Application No. 61/696,862, filed on Sep. 5, 2012. The priority of both said PCT and U.S. Provisional Patent Application are claimed. Each of prior mentioned applications is hereby incorporated by reference herein in its entirety.

The present invention relates to organic compounds useful for therapy and/or prophylaxis in a mammal of an inflammatory disease or disorder, and in particular to substituted cyanopyrazole compounds, their manufacture, pharmaceutical compositions containing them and their use as lysophosphatidic acid (LPA) antagonists.

All documents cited to or relied upon below are expressly incorporated herein by reference.

LPA is a family of bioactive phosphate lipids which function like a growth factor mediator by interacting with LPA receptors, a family of G-protein-coupled receptors (GPCRs). The lipid family has long chain saturated (such as C18:0 or C16:0) or unsaturated (C18:1 or C20:4) carbon chains attached to the glycerol through an ester linkage. In biological systems, LPA is produced by multi-step enzymatic pathways through the de-esterification of membrane phospholipids. Enzymes that contribute to LPA synthesis include lysophospholipase D (lysoPLD), autotaxin (ATX), phospholipase A1 (PLAT), phospholipase A2 (PLA2) and acylglycerol kinase (AGK) (British J. of Pharmacology 2012, 165, 829-844).

There are at least six LPA receptors identified (LPAR1-6). LPA signaling exerts a broad range of biological responses on many different cell types, which can lead to cell growth, cell proliferation, cell migration and cell contraction. Up regulation of the LPA pathway has been linked to multiple diseases, including cancer, allergic airway inflammation, and fibrosis of the kidney, lung and liver. Therefore, targeting LPA receptors or LPA metabolic enzymes could provide new approaches towards the treatment of medically important diseases that include neuropsychiatric disorders, neuropathic pain, infertility, cardiovascular disease, inflammation, fibrosis, and cancer (Annu Rev. Pharmacol. Toxicol. 2010, 50, 157-186; J. Biochem. 2011, 150, 223-232).

Fibrosis is the result of an uncontrolled tissue healing process leading to excessive accumulation of extracellular matrix (ECM). Recently it was reported that the LPA1 receptor was over expressed in idiopathic pulmonary fibrosis (IPF) patients. Mice with LPA1 receptor knockout were protected from bleomycin-induced lung fibrosis (Nature Medicine 2008, 14, 45-54). Thus, antagonizing the LPA1 receptor may be useful for the treatment of fibrosis, such as renal fibrosis, pulmonary fibrosis, arterial fibrosis and systemic sclerosis.

In an embodiment of the present invention, provided are compounds of general Formula (I):

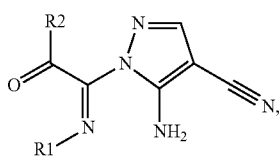

(I)

wherein
R1 is lower alkyl or cycloalkyl; and
R2 is phenyl, unsubstituted or mono-, bi- or tri-substituted independently with alkoxy, phenyl-alkoxy, lower alkyl or halogen; naphthalenyl, unsubstituted or substituted with alkoxy; or indenyl, unsubstituted or substituted with alkoxy; or a pharmaceutically acceptable salt thereof.

In a further embodiment of the invention, provided is a pharmaceutical composition comprising a therapeutically effective amount of a compound according to formula (I) and a therapeutically inert carrier.

In a still further embodiment of the invention, provided is a method for the treatment or prophylaxis of pulmonary fibrosis, which method comprises the step of administering a therapeutically effective amount of a compound according to formula (I) to a patient in need thereof.

Unless otherwise indicated, the following specific terms and phrases used in the description and claims are defined as follows:

As used herein, the term "alkyl", alone or in combination with other groups, refers to a branched or straight-chain monovalent saturated aliphatic hydrocarbon radical of one to twenty carbon atoms, preferably one to sixteen carbon atoms, more preferably one to ten carbon atoms. The term "lower alkyl", alone or in combination with other groups, refers to a branched or straight-chain alkyl radical of one to nine carbon atoms, preferably one to six carbon atoms, more preferably one to four carbon atoms. This term is further exemplified by radicals such as methyl, ethyl, n-propyl, isopropyl, n-butyl, s-butyl, isobutyl, t-butyl, n-pentyl, 3-methylbutyl, n-hexyl, 2-ethylbutyl and the like.

The term "cycloalkyl" refers to a monovalent mono- or polycarbocyclic radical of three to ten, preferably three to six carbon atoms. This term is further exemplified by radicals such as cyclopropyl, cyclobutyl, cyclopentyl, cyclohexyl, cycloheptyl, norbornyl, adamantyl and the like. In a preferred embodiment, the "cycloalkyl" moieties can optionally be substituted with one, two, three or four substituents, with the understanding that said substituents are not, in turn, substituted further. Each substituent can independently be, e.g., alkyl, alkoxy, halogen, amino, hydroxyl or oxygen (O=) unless otherwise specifically indicated. Examples of cycloalkyl moieties include, but are not limited to, optionally substituted cyclopropyl, optionally substituted cyclobutyl, optionally substituted cyclopentyl, optionally substituted cyclopentenyl, optionally substituted cyclohexyl, optionally substituted cyclohexylene, optionally substituted cycloheptyl, and the like or those which are specifically exemplified herein.

The alkyl and lower alkyl groups described above may be substituted independently with one, two, or three substituents, with the understanding that said substituents are not, in turn, substituted further. Substituents may include, e.g., halogen, lower alkyl, —CF$_3$, —SO$_2$CH$_3$, alkoxy, —C(O)CH$_3$, —OH, —SCH$_3$ and —CH$_2$CH$_2$OH.

As used herein, the term "alkoxy" means alkyl-O—; and "alkoyl" means alkyl-CO—. Alkoxy substituent groups or alkoxy-containing substituent groups may be substituted by, e.g., one or more alkyl or phenyl groups, with the understanding that said substituents are not, in turn, substituted further.

As used herein, the term "halogen" means a fluorine, chlorine, bromine or iodine radical, preferably a fluorine, chlorine or bromine radical, and more preferably a fluorine or bromine radical.

Compounds of formula I can have one or more asymmetric carbon atoms and can exist in the form of optically pure enantiomers, mixtures of enantiomers such as, e.g., racemates, optically pure diastereoisomers, mixtures of diastereoisomers, diastereoisomeric racemates or mixtures of diastereoisomeric racemates. The optically active forms can be obtained e.g. by resolution of the racemates, by asymmetric synthesis or asymmetric chromatography (chromatography with a chiral adsorbents or eluant). The invention embraces all of these forms.

As used herein, the term "pharmaceutically acceptable salt" means any pharmaceutically acceptable salt of the compound of formula (I). Salts may be prepared from pharmaceutically acceptable non-toxic acids and bases including inorganic and organic acids and bases. Such acids include, e.g., acetic, benzenesulfonic, benzoic, camphorsulfonic, citric, ethenesulfonic, dichloroacetic, formic, fumaric, gluconic, glutamic, hippuric, hydrobromic, hydrochloric, isethionic, lactic, maleic, malic, mandelic, methanesulfonic, mucic, nitric, oxalic, pamoic, pantothenic, phosphoric, succinic, sulfuric, tartaric, oxalic, p-toluenesulfonic and the like. Particularly preferred are fumaric, hydrochloric, hydrobromic, phosphoric, succinic, sulfuric and methanesulfonic acids. Acceptable base salts include alkali metal (e.g. sodium, potassium), alkaline earth metal (e.g. calcium, magnesium) and aluminum salts.

In the practice of the method of the present invention, an effective amount of any one of the compounds of this invention or a combination of any of the compounds of this invention or a pharmaceutically acceptable salt thereof, is administered via any of the usual and acceptable methods known in the art, either singly or in combination. The compounds or compositions can thus be administered orally (e.g., buccal cavity), sublingually, parenterally (e.g., intramuscularly, intravenously, or subcutaneously), rectally (e.g., by suppositories or washings), transdermally (e.g., skin electroporation) or by inhalation (e.g., by aerosol), and in the form or solid, liquid or gaseous dosages, including tablets and suspensions. The administration can be conducted in a single unit dosage form with continuous therapy or in a single dose therapy ad libitum. The therapeutic composition can also be in the form of an oil emulsion or dispersion in conjunction with a lipophilic salt such as pamoic acid, or in the form of a biodegradable sustained-release composition for subcutaneous or intramuscular administration.

Useful pharmaceutical carriers for the preparation of the compositions hereof, can be solids, liquids or gases. Thus, the compositions can take the form of tablets, pills, capsules, suppositories, powders, enterically coated or other protected formulations (e.g. binding on ion-exchange resins or packaging in lipid-protein vesicles), sustained release formulations, solutions, suspensions, elixirs, aerosols, and the like. The carrier can be selected from the various oils including those of petroleum, animal, vegetable or synthetic origin, e.g., peanut oil, soybean oil, mineral oil, sesame oil, and the like. Water, saline, aqueous dextrose, and glycols are preferred liquid carriers, particularly (when isotonic with the blood) for injectable solutions. For example, formulations for intravenous administration comprise sterile aqueous solutions of the active ingredient(s) which are prepared by dissolving solid active ingredient(s) in water to produce an aqueous solution, and rendering the solution sterile. Suitable pharmaceutical excipients include starch, cellulose, talc, glucose, lactose, talc, gelatin, malt, rice, flour, chalk, silica, magnesium stearate, sodium stearate, glycerol monostearate, sodium chloride, dried skim milk, glycerol, propylene glycol, water, ethanol, and the like. The compositions may be subjected to conventional pharmaceutical additives such as preservatives, stabilizing agents, wetting or emulsifying agents, salts for adjusting osmotic pressure, buffers and the like. Suitable pharmaceutical carriers and their formulation are described in Remington's Pharmaceutical Sciences by E. W. Martin. Such compositions will, in any event, contain an effective amount of the active compound together with a suitable carrier so as to prepare the proper dosage form for proper administration to the recipient.

The dose of a compound of the present invention depends on a number of factors, such as, e.g., the manner of administration, the age and the body weight of the subject, and the condition of the subject to be treated, and ultimately will be decided by the attending physician or veterinarian. Such an amount of the active compound as determined by the attending physician or veterinarian is referred to herein, and in the claims, as a "therapeutically effective amount". For example, the dose of a compound of the present invention is typically in the range of about 1 to about 1000 mg per day. Preferably, the therapeutically effective amount is in an amount of from about 1 mg to about 500 mg per day.

The present invention provides for compounds having the general formula (I):

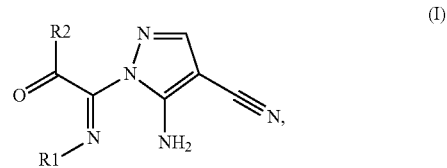

wherein
R1 is lower alkyl or cycloalkyl; and
R2 is phenyl, unsubstituted or mono-, bi- or tri-substituted independently with alkoxy, phenyl-alkoxy, lower alkyl or halogen; naphthalenyl, unsubstituted or substituted with alkoxy; or indenyl, unsubstituted or substituted with alkoxy; or a pharmaceutically acceptable salt thereof.

In another embodiment of the invention, provided is a compound of formula (I), wherein R1 is methyl, propyl, isopropyl or tert-butyl.

In another embodiment of the invention, provided is a compound of formula (I), wherein R1 is cyclopentyl or cyclohexyl.

In another embodiment of the invention, provided is a compound of formula (I), wherein R2 is unsubstituted phenyl.

In another embodiment of the invention, provided is a compound of formula (I), wherein R2 is phenyl mono-substituted with ethyl, bromo, fluoro or methoxy.

In another embodiment of the invention, provided is a compound of formula (I), wherein R2 is phenyl di-substituted independently with methoxy, benzyloxy or fluoro.

In another embodiment of the invention, provided is a compound of formula (I), wherein R2 is phenyl tri-substituted with methoxy.

In another embodiment of the invention, provided is a compound of formula (I), wherein R2 is naphthalenyl substituted with methoxy.

In another embodiment of the invention, provided is a compound of formula (I), wherein R2 is indenyl substituted with methoxy.

In another embodiment of the invention, provided is a compound of formula (I) wherein said compound is:
(E)-5-Amino-1-(1-(cyclopentylimino)-2-(2,4-dimethoxyphenyl)-2-oxoethyl)-1H-pyrazole-4-carbonitrile;
(E)-5-Amino-1-(1-(cyclopentylimino)-2-(4-ethylphenyl)-2-oxoethyl)-1H-pyrazole-4-carbonitrile;

(E)-5-Amino-1-(1-(cyclopentylimino)-2-(4-bromophenyl)-2-oxo ethyl)-1H-pyrazole-4-carbonitrile;
(E)-5-Amino-1-(1-(cyclopentylimino)-2-(4-fluoro-2-methoxyphenyl)-2-oxo ethyl)-1H-pyrazole-4-carbonitrile;
(E)-5-Amino-1-(1-(cyclopentylimino)-2-(2-fluoro-4-methoxyphenyl)-2-oxo ethyl)-1H-pyrazole-4-carbonitrile;
(E)-5-Amino-1-(1-(cyclopentylimino)-2-(2,4,5-trimethoxyphenyl)-2-oxo ethyl)-1H-pyrazole-4-carbonitrile;
(E)-5-Amino-1-(1-(cyclopentylimino)-2-(3-methoxynaphthalen-2-yl)-2-oxo ethyl)-1H-pyrazole-4-carbonitrile;
(E)-5-Amino-1-(1-(cyclopentylimino)-2-(6-methoxy-2,3-dihydro-1H-inden-5-yl)-2-oxo ethyl)-1H-pyrazole-4-carbonitrile;
(E)-5-Amino-1-(1-(cyclohexylimino)-2-(2,4-dimethoxyphenyl)-2-oxo ethyl)-1H-pyrazole-4-carbonitrile;
(E)-5-Amino-1-(2-(2,4-dimethoxyphenyl)-1-(iso-propylimino)-2-oxo ethyl)-1H-pyrazole-4-carbonitrile;
(E)-5-Amino-1-(2-(4-benzyloxy-2-methoxyphenyl)-1-(cyclopentylimino)-2-oxo ethyl)-1H-pyrazole-4-carbonitrile; or
(E)-5-Amino-1-(1-(cyclopentylimino)-2-(3,4,5-trimethoxyphenyl)-2-oxo ethyl)-1H-pyrazole-4-carbonitrile.

In another embodiment of the invention, provided is a compound of formula (I) for use as a therapeutically active substance.

In another embodiment of the invention, provided is a pharmaceutical composition comprising a therapeutically effective amount of a compound of formula (I) and a therapeutically inert carrier.

In another embodiment of the invention, provided is a use of a compound according to formula (I) for the treatment or prophylaxis of pulmonary fibrosis.

In another embodiment of the invention, provided is a use of a compound according to formula (I) for the preparation of a medicament for the treatment or prophylaxis of pulmonary fibrosis.

In another embodiment of the invention, provided is a compound according to formula (I) for the treatment or prophylaxis of pulmonary fibrosis.

In another embodiment of the invention, provided is compound according formula (I), when manufactured according to a process below.

In another embodiment of the invention, provided is a method for the treatment or prophylaxis of pulmonary fibrosis, which method comprises the step of administering a therapeutically effective amount of a compound of formula (I) to a patient in need thereof.

In another embodiment of the invention, provided is an invention as hereinbefore described.

It will be appreciated, that the compounds of general formula I in this invention may be derivatized at functional groups to provide derivatives which are capable of conversion back to the parent compound in vivo. Physiologically acceptable and metabolically labile derivatives, which are capable of producing the parent compounds of general formula I in vivo are also within the scope of this invention.

Compounds of the present invention can be prepared beginning with commercially available starting materials, or utilizing general synthetic techniques and procedures known to those skilled in the art. Chemicals may be purchased from companies such as e.g. Aldrich, Argonaut Technologies, VWR, Lancaster, Princeton, Alfa, Oakwood, TCI, Fluorochem, Apollo, Matrix, Maybridge or Meinoah. Chromatography supplies and equipment may be purchased from such companies as e.g. AnaLogix, Inc, Burlington, Wis.; Biotage AB, Charlottesville, Va.; Analytical Sales and Services, Inc., Pompton Plains, N.J.; Teledyne Isco, Lincoln, Nebr.; VWR International, Bridgeport, N.J.; Varian Inc., Palo Alto, Calif., and Multigram II Mettler Toledo Instrument Newark, Del. Biotage, ISCO and Analogix columns are pre-packed silica gel columns used in standard chromatography. Final compounds and intermediates were named using the AutoNom2000 feature in the MDL ISIS Draw application.

The present invention is also directed to the administration of a therapeutically effective amount of a compound of formula I in combination or association with other drugs or active agents for the treatment of inflammatory or allergic diseases and disorders. In one embodiment, the present invention relates to a method for the treatment and/or prevention of such diseases or disorders comprising administering to a human or animal simultaneously, sequentially, or separately, a therapeutically effective amount of a compound of formula I and another drug or active agent (such as another anti-inflammatory or anti-allergic drug or agent). These other drugs or active agents may have the same, similar, or a completely different mode of action. Suitable other drugs or active agents may include, but are not limited to: Beta2-adrenergic agonists such as albuterol or salmeterol; corticosteroids such as dexamethasone or fluticasone; antihistamines such as loratidine; leukotriene antagonists such as montelukast or zafirlukast; anti-IgE antibody therapies such as omalizumab; anti-infectives such as fusidic acid (particularly for the treatment of atopic dermatitis); anti-fungals such as clotrimazole (particularly for the treatment of atopic dermatitis); immunosuppressants such as tacrolimus and pimecrolimus; other antagonists of PGD2 acting at other receptors such as DP antagonists; inhibitors of phosphodiesterase type 4 such as cilomilast; drugs that modulate cytokine production such as inhibitors of TNF-alpha converting enzyme (TACE); drugs that modulate the activity of Th2 cytokines IL-4 and IL-5 such as blocking monoclonal antibodies and soluble receptors; PPAR-gamma agonists such as rosiglitazone; and 5-lipoxygenase inhibitors such as zileuton.

The compounds of the present invention can be prepared by any conventional means. Suitable processes for synthesizing these compounds are provided in the examples. Generally, compounds of formula I can be prepared according to scheme 1 illustrated below.

Scheme 1

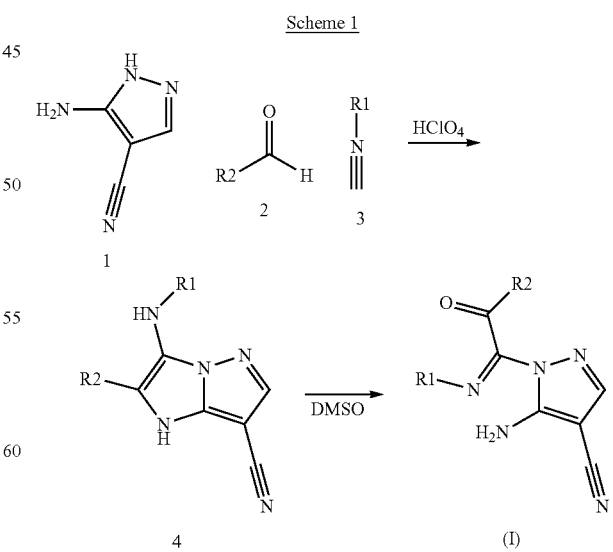

The commercially available 5-amino-1H-pyrazole-4-carbonitrile (1) can react with aldehyde (2) and isonitrile (3)

under the acidic condition to form compound (4). This reaction can be carried out according to the literature procedure (Angew. Chem. Int. Ed. 1998, 37, 2234-2237). Compound 4 can be oxidized and then hydrolyzed to form compound (I) in DMSO. R1 can be, e.g., lower alkyl or cycloalkyl. R2 can be, e.g., unsubstituted phenyl, substituted phenyl, unsubstituted naphthalenyl, substituted naphthalenyl, unsubstituted indenyl or substituted indenyl.

EXAMPLES

Although certain exemplary embodiments are depicted and described herein, the compounds of the present invention can be prepared using appropriate starting materials according to the methods described generally herein and/or by methods available to one of ordinary skill in the art.

Example 1

(E)-5-Amino-1-(1-(cyclopentylimino)-2-(2,4-dimethoxyphenyl)-2-oxoethyl)-1H-pyrazole-4-carbonitrile

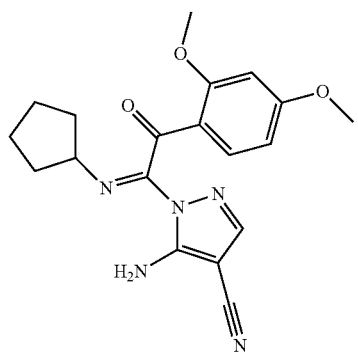 [SMILES: COc1ccc(C(=O)/C(=N\C2CCCC2)n2ncc(C#N)c2N)c(OC)c1]

Step 1: Preparation of 3-(cyclopentylamino)-2-(2,4-dimethoxyphenyl)-1H-imidazo[1,2-b]pyrazole-7-carbonitrile To a clear light brown solution of 2,4-dimethoxybenzaldehyde (1.0 g, 6.02 mmol) and 5-amino-1H-pyrazole-4-carbonitrile (651 mg, 6.02 mmol) in methanol (21 mL) in a 50 mL sealed tube were added cyclopentane isonitrile (579 mg, 673 µL, 6.02 mmol) and perchloric acid (121 mg, 108 µL, 1.2 mmol) at RT under nitrogen atmosphere. Then, the nitrogen line was disconnected and the flask was sealed with a cap. The resulting dark brown solution slowly became a suspension within 10 minutes which was then stirred for 15 h at room temperature (RT). The off-white solids were collected by filtration and washed with methanol. After air drying, 1.09 g (51.5%) of 3-(cyclopentylamino)-2-(2,4-dimethoxyphenyl)-1H-imidazo[1,2-b]pyrazole-7-carbonitrile was isolated as an off-white solid. LC/MS calcd. for $C_{19}H_{21}N_5O_2$ (m/e) 351.408, obsd. 352.2 (M+H, ES+).

Step 2: Preparation of (E)-5-amino-1-(1-(cyclopentylimino)-2-(2,4-dimethoxyphenyl)-2-oxoethyl)-1H-pyrazole-4-carbonitrile A light brown solution of 3-(cyclopentylamino)-2-(2,4-dimethoxyphenyl)-1H-imidazo[1,2-b]pyrazole-7-carbonitrile (1.09 g, 3.1 mmol) in DMSO (200 mL) was stored for 35 days at RT. Within 24 h, it became a dark brown solution. After 35 days, LC/MS analysis indicated the absence of starting material and the presence of a strong desired peak. Then, it was poured into water (1 L) and the resulting cloudy brown solution was extracted with ethyl acetate (2×200 mL). Then, the combined extracts were washed with water and brine solution (2 L) to remove the DMSO. The organic layer was dried over anhydrous $MgSO_4$, filtered, and concentrated to give the red brown paste (1.25 g) which was purified using an ISCO (150 g) column chromatography eluting with 0-40% ethyl acetate in hexanes. The desired fractions were combined and the solvent was removed under vacuum to obtain 224 mg (19.7% yield) of (E)-5-amino-1-(1-(cyclopentylimino)-2-(2,4-dimethoxyphenyl)-2-oxoethyl)-1H-pyrazole-4-carbonitrile as an off-white solid. $^1$H NMR (400 MHz, DMSO-$d_6$) δ: 1.40-1.85 (br m, 8H), 3.66 (m, 1H), 3.66 (s, 3H), 3.87 (s, 3H), 6.62 (d, J=2.4 Hz, 1H), 6.71 (dd, J=2.4 and 9.0 Hz, 1H), 7.63 (s, 1H), 7.86 (d, J=9.0 Hz, 1H), 8.05 (brs, 2H). LC/MS calcd. for $C_{19}H_{21}N_5O_3$ (m/e) 367.4, obsd. 368.0 (M+H, ES+).

Example 2

(E)-5-Amino-1-(1-(cyclopentylimino)-2-(4-ethylphenyl)-2-oxoethyl)-1H-pyrazole-4-carbonitrile

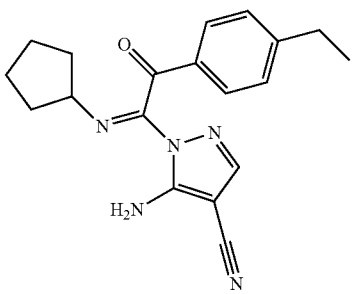 [SMILES: CCc1ccc(C(=O)/C(=N\C2CCCC2)n2ncc(C#N)c2N)cc1]

Step 1: Preparation of 3-(cyclopentylamino)-2-(4-ethylphenyl)-1H-imidazo[1,2-b]pyrazole-7-carbonitrile To a clear colorless solution of 5-amino-1H-pyrazole-4-carbonitrile (161 mg, 1.49 mmol) in methanol (3 mL) were added 4-ethylbenzaldehyde (200 mg, 204 µL, 1.49 mmol) followed by cyclopentyl isonitrile (143 mg, 167 µL, 1.49 mmol) and perchloric acid (29.9 mg, 26.7 µL, 0.298 mmol) at RT under nitrogen atmosphere. The resulting brown solution was stirred for 15 h and during this period (within 5 min) lot of solids were formed. The solids were collected by filtration and washed with methanol. After air drying, 88 mg (18.5% yield) of 3-(cyclopentylamino)-2-(4-ethylphenyl)-1H-imidazo[1,2-b]pyrazole-7-carbonitrile was isolated as an off-white solid. LC/MS calcd. for $C_{19}H_{21}N_5$ (m/e) 319.4, obsd. 320.1 (M+H, ES+).

Step 2: Preparation of (E)-5-amino-1-(1-(cyclopentylimino)-2-(4-ethylphenyl)-2-oxoethyl)-1H-pyrazole-4-carbonitrile A light brown solution of 3-(cyclopentylamino)-2-(4-ethylphenyl)-1H-imidazo[1,2-b]pyrazole-7-carbonitrile (56.4 mg, 0.177 mmol) in DMSO (17.7 mL) was stored for 35 days at RT. Within 24 h, it became a dark brown solution. After 35 days, LCMS analysis indicated the absence of starting material and the presence of a strong desired peak. Then, it was poured into water (1 L) and the resulting cloudy brown solution was extracted with EA (2×200 mL). Then, the combined extracts were washed with water and brine solution (2 L) to wash the DMSO. The organic layer was dried over anhydrous MgSO$_4$, filtered, and concentrated to give the red brown paste which was purified using an ISCO (120 g) column chromatography eluting with 0-40% ethyl acetate in hexanes. The desired fractions were combined and the solvent was removed under vacuum to obtain 5.9 mg (10% yield) of (E)-5-amino-1-(1-(cyclopentylimino)-2-(4-ethylphenyl)-2-oxoethyl)-1H-pyrazole-4-carbonitrile as an off-white solid. $^1$H NMR (400 MHz, CDCl$_3$) δ: 1.28 (t, J=7.7 Hz, 3H), 1.40-2.00 (br m, 8H), 2.75 (q, J=7.7 Hz, 2H), 3.78 (p, J=6.1 Hz, 1H), 6.78 (br s, 2H), 7.36 (d, J=8.3 Hz, 2H), 7.42 (s, 1H), 7.81 (d, J=8.3 Hz, 2H). LC/MS calcd. for C$_{19}$H$_{21}$N$_5$O$_3$ (m/e) 367.4, obsd. 368.0 (M+H, ES+).

Example 3

(E)-5-Amino-1-(1-(cyclopentylimino)-2-(4-bromophenyl)-2-oxoethyl)-1H-pyrazole-4-carbonitrile

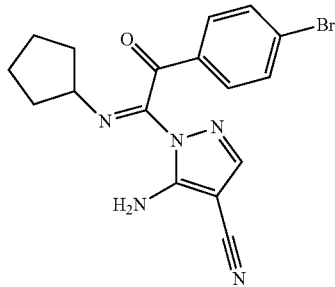 [SMILES: N#Cc1cnn(/C(=N/C2CCCC2)C(=O)c2ccc(Br)cc2)c1N]

Step 1: Preparation of 3-(cyclopentylamino)-2-(4-bromophenyl)-1H-imidazo[1,2-b]pyrazole-7-carbonitrile To a clear colorless solution of 4-bromobenzaldehyde (3.71 g, 20.1 mmol) and 5-amino-1H-pyrazole-4-carbonitrile (2.17 g, 20.1 mmol) in a 350 mL sealed tube in methanol (70 mL) were added cyclopentane isonitrile (1.93 g, 2.24 mL, 20.1 mmol) and perchloric acid (403 mg, 360 µL, 4.01 mmol) at RT under nitrogen atmosphere. Then, the nitrogen line was disconnected and the flask was sealed with a cap. The resulting light yellow solution slowly became a suspension within 5 minutes which was then stirred for 15 h at RT. The off-white solids were collected by filtration and washed with methanol. After air drying, 5.1 g (68.7% yield) of 3-(cyclopentylamino)-2-(4-bromophenyl)-1H-imidazo[1,2-b]pyrazole-7-carbonitrile was isolated as an off-white solid. LC/MS calcd. for C$_{17}$H$_{16}$BrN$_5$ (m/e) 370.25, obsd. 372.0 (M+H, ES+).

Step 2: Preparation of (E)-5-amino-1-(1-(cyclopentylimino)-2-(4-bromophenyl)-2-oxoethyl)-1H-pyrazole-4-carbonitrile A dilute solution of 2-(4-bromophenyl)-3-(cyclopentylamino)-1H-imidazo[1,2-b]pyrazole-7-carbonitrile (500 mg, 1.35 mmol) in DMSO (100 mL) was stored at RT for more than 60 days. The yellow DMSO solution was poured into water (1 L) and the organic compound was extracted into ethyl acetate (2×75 mL). The combined extracts were washed with water and brine solution. The organic layer was dried over anhydrous MgSO$_4$, filtered and concentrated to give the crude yellow solid which was not soluble in dichloromethane even at hot condition. Then, after cooling to RT, the solids were collected by filtration and washed with dichloromethane and the $^1$H NMR of this solid indicated that it is mostly starting material. Whereas, the mother liquor was removed under vacuum and the crude residue was purified using an ISCO (80 g) column eluting with 0-35% ethyl acetate in hexanes. The pure fractions were combined and the solvent was removed under vacuum to obtain 113 mg (21.7% yield) of (E)-5-amino-1-(1-(cyclopentylimino)-2-(4-bromophenyl)-2-oxoethyl)-1H-pyrazole-4-carbonitrile as a light yellow solid. $^1$H NMR (400 MHz, DMSO-d$_6$) δ: 1.40-1.80 (br m, 8H), 3.63 (p, 1H), 7.72 (s, 1H), 7.78 (d, J=6.1 Hz, 2H), 7.83 (d, J=6.2 Hz, 2H), 8.14 (br s, 2H). LC/MS calcd. for C$_{17}$H$_{16}$BrN$_5$O (m/e) 386.25, obsd. 387.2 (M+H, ES+).

Example 4

(E)-5-Amino-1-(1-(cyclopentylimino)-2-(4-fluoro-2-methoxyphenyl)-2-oxoethyl)-1H-pyrazole-4-carbonitrile

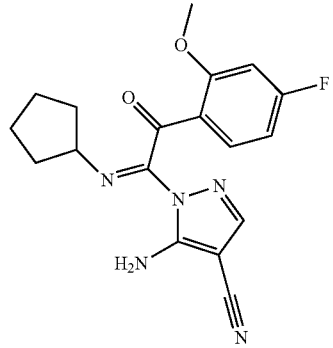 [SMILES: COc1cc(F)ccc1C(=O)/C(=N\C1CCCC1)n1ncc(C#N)c1N]

Step 1: Preparation of 3-(cyclopentylamino)-2-(4-fluoro-2-methoxyphenyl)-1H-imidazo[1,2-b]pyrazole-7-carbonitrile To a clear light yellow solution of 5-amino-1H-pyrazole-4-carbonitrile (169 mg, 1.56 mmol) and 4-fluoro-2-methoxybenzaldehyde (240 mg, 1.56 mmol) in methanol (3 mL) was added cyclopentane isonitrile (150 mg, 174 µL, 1.56 mmol) followed by perchloric acid (31.3 mg, 28.0 µL, 0.312 mmol) at RT under nitrogen atmosphere. The resulting light brown suspension was stirred for 15 h and during this period (within 1 minute) lot of solids were formed. The solids were collected by filtration and washed with methanol. After air drying, 175 mg (33% yield) of 3-(cyclopentylamino)-2-(4-fluoro-2-methoxyphenyl)-1H-imidazo[1,2-b]pyrazole-7-carbonitrile was isolated as an off-white solid. LC/MS calcd. for C$_{18}$H$_{18}$FN$_5$O (m/e) 339.37, obsd. 340.0 (M+H, ES+).

Step 2: Preparation of (E)-5-Amino-1-(1-(cyclopentylimino)-2-(4-fluoro-2-methoxyphenyl)-2-oxoethyl)-1H-pyrazole-4-carbonitrile A light yellow solution of 3-(cyclopentylamino)-2-(4-fluoro-2-methoxyphenyl)-1H-imidazo[1,2-b]pyrazole-7- carbonitrile (130 mg, 0.383 mmol) in DMSO (5 mL) was kept at RT in a 10 mL vial. The resulting light yellow solution was stored for 60 days. Then, the crude compound in DMSO was purified by using an HPLC column chromatography using acetonitrile and ammonium acetate as eluent. The desired peak was collected and the solvent was removed under vacuum to obtain 48 mg (35% yield) of (E)-5-Amino-1-(1-(cyclopentylimino)-2-(4-fluoro-2-methoxyphenyl)-2-oxoethyl)-1H-pyrazole-4-carbonitrile as an off-white solid. $^1$H NMR (400 MHz, DMSO-$d_6$) δ: 1.40-1.62 (br m, 4H), 1.62-1.78 (br, 4H), 3.67 (p, 1H), 3.70 (s, 3H), 7.01 (dt, 1H), 7.13 (dd, 1H), 7.66 (s, 1H), 7.99 (dd, 1H), 8.06 (brvs, 2H). LC/MS calcd. for $C_{18}H_{18}FN_5O_2$ (m/e) 355.371, obsd. 355.9 (M+H, ES+).

it was poured into water (300 mL) and the organic compound was extracted into ethyl acetate (3×50 mL). The combined organic extracts were washed with brine solution and dried over anhydrous $MgSO_4$. Filtration and concentration gave the crude yellow solid which was purified using an ISCO (80 g) column chromatography eluting with 0-50% ethyl acetate in hexanes. The desired fractions were combined and the solvent was removed under vacuum to isolate 32 mg (15.4% yield) of (E)-5-amino-1-(1-(cyclopentylimino)-2-(2-fluoro-4-methoxyphenyl)-2-oxo ethyl)-1H-pyrazole-4-carbonitrile as an yellow solid. $^1$H NMR (400 MHz, DMSO-$d_6$) δ: 1.45-1.53 (br m, 4H), 1.53-1.85 (br m, 4H), 3.73 (p, 1H), 3.89, (s, 3H), 6.95-7.10 (m, 2H), 7.72 (s, 1H), 7.92 (t, J=8.5 Hz, 1H), 8.11 (br s, 2H). LC/MS calcd. for $C_{18}H_{18}FN_5O_2$ (m/e) 355.371, obsd. 356.2 (M+H, ES+).

Example 5

(E)-5-Amino-1-(1-(cyclopentylimino)-2-(2-fluoro-4-methoxyphenyl)-2-oxoethyl)-1H-pyrazole-4-carbonitrile Example 6

(E)-5-Amino-1-(1-(cyclopentylimino)-2-(2,4,5-trimethoxyphenyl)-2-oxoethyl)-1H-pyrazole-4-carbonitrile

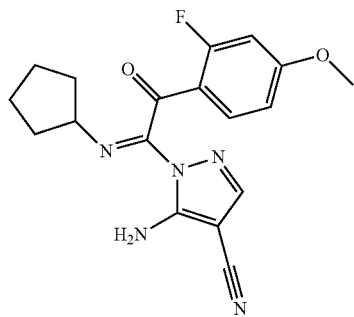 [SMILES: COc1ccc(C(=O)/C(=N\C2CCCC2)n2ncc(C#N)c2N)c(F)c1]

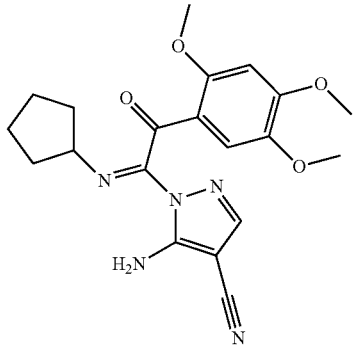 [SMILES: COc1cc(OC)c(C(=O)/C(=N\C2CCCC2)n2ncc(C#N)c2N)cc1OC]

Step 1: Preparation of 3-(cyclopentylamino)-2-(2-fluoro-4-methoxyphenyl)-1H-imidazo[1,2-b]pyrazole-7-carbonitrile To a clear light yellow solution of 2-fluoro-4-methoxybenzaldehyde (802 mg, 5.2 mmol) and 5-amino-1H-pyrazole-4-carbonitrile (562 mg, 5.2 mmol) in methanol (20 mL) were added a neat cyclopentyl isonitrile (500 mg, 5.2 mmol) and perchloric acid (104 mg, 93.3 μL, 1.04 mmol) at RT under nitrogen atmosphere. Lots of brown solids were precipitated within 1 h and the resulting suspension was stirred for 15 h. After 15 h, it became a dark brown solution without any solids. Then, the solvent was removed under vacuum and the residue was purified using an ISCO (120 g) column chromatography eluting with 0-50% EA in hexanes. The desired fractions were combined and the solvent was removed under vacuum to obtain 203 mg (11.5% yield) of 3-(cyclopentylamino)-2-(2-fluoro-4-methoxyphenyl)-1H-imidazo[1,2-b]pyrazole-7-carbonitrile as an yellow solid. LC/MS calcd. for $C_{18}H_{18}FN_5O$ (m/e) 339.37, obsd. 340.2 (M+H, ES+).

Step 2: Preparation of (E)-5-Amino-1-(1-(cyclopentylimino)-2-(2-fluoro-4-methoxyphenyl)-2-oxoethyl)-1H-pyrazole-4-carbonitrile A light yellow solution of 3-(cyclopentylamino)-2-(2-fluoro-4-methoxyphenyl)-1H-imidazo[1,2-b]pyrazole-7-carbonitrile (199 mg, 0.586 mmol) in DMSO (100 mL) was stored for several days at RT. After 2 days, it became a light brown solution and this solution was stored for 50 days. Then, Step 1: Preparation of 3-(cyclopentylamino)-2-(2,4,5-trimethoxyphenyl)-1H-imidazo[1,2-b]pyrazole-7-carbonitrile To a clear light brown solution of 2,4,5-trimethoxybenzaldehyde (600 mg, 3.06 mmol) and 5-amino-1H-pyrazole-4-carbonitrile (331 mg, 3.06 mmol) in methanol (10 mL) in a 20 mL vial were added cyclopentyl isonitrile (294 mg, 342 μL, 3.06 mmol) and perchloric acid (61.4 mg, 54.9 μL, 0.612 mmol) at RT under nitrogen atmosphere. Then, the nitrogen line was disconnected and the resulting dark brown solution slowly became a suspension within few hours which was then stirred for 15 h at RT. The off-white solids were collected by filtration and washed with methanol and the solids were not the desired product. The filtrate was removed under vacuum and the resulting residue was purified using an ISCO (120 g) column chromatography eluting with 0-60% ethyl acetate in hexanes. The desired fractions were combined and the solvent was removed under vacuum to isolate 165 mg (14% yield) of 3-(cyclopentylamino)-2-(2,4,5-trimethoxyphenyl)-1H-imidazo[1,2-b]pyrazole-7-carbonitrile as a dark brown solid. LC/MS calcd. for $C_{20}H_{23}N_5O_3$ (m/e) 381.434, obsd. 382.1 (M+H, ES+).

Step 2: Preparation of (E)-5-amino-1-(1-(cyclopentylimino)-2-(2,4,5-trimethoxyphenyl)-2-oxoethyl)-1H-pyrazole-4-carbonitrile A mixture of 3-(cyclopentylamino)-2-(2,4,5-trimethoxyphenyl)-1H-imidazo[1,2-b]pyrazole-7-carbonitrile (153 mg, 0.401 mmol) and DMSO (20 mL) was heated gently to dissolve all the solids. The resulting brown solution was stored for 30 days at RT. As a result, some solids were precipitated which was collected by filtration and the filtrate was diluted with water (~100 mL). The resulting solids were collected by filtration and washed with diethyl ether. These solids were again purified by HPLC using acetonitrile and ammonium acetate as eluent to obtain 16.5 mg (10% yield) of (E)-5-amino-1-(1-(cyclopentylimino)-2-(2,4,5-trimethoxyphenyl)-2-oxoethyl)-1H-pyrazole-4-carbonitrile as a brown solid. $^1$H NMR (400 MHz, DMSO-$d_6$) δ: 1.40-1.85 (br m, 8H), 3.65 (s, 3H), 3.67 (p, 1H), 3.79 (s, 3H), 3.91 (s, 3H), 6.72 (s, 1H), 7.35 (s, 1H), 7.63 (s, 1H), 8.06 (br s, 2H). LC/MS calcd. for $C_{20}H_{23}N_5O_4$ (m/e) 397.433, obsd. 398.3 (M+H, ES+).

Example 7

(E)-5-Amino-1-(1-(cyclopentylimino)-2-(3-methoxynaphthalen-2-yl)-2-oxoethyl)-1H-pyrazole-4-carbonitrile

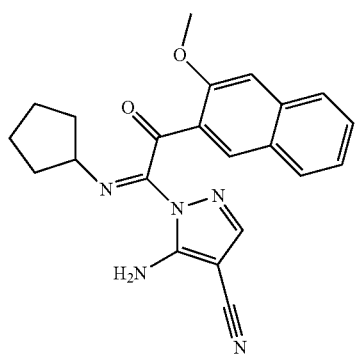 [SMILES: COc1cc2ccccc2cc1C(=O)/C(=N\C1CCCC1)n1ncc(C#N)c1N]

Step 1: Preparation of 3-(cyclopentylamino)-2-(3-methoxynaphthalen-2-yl)-1H-imidazo[1,2-b]pyrazole-7-carbonitrile To a clear solution of 3-methoxy-2-naphthaldehyde (484 mg, 2.6 mmol) and 5-amino-1H-pyrazole-4-carbonitrile (281 mg, 2.6 mmol) in methanol (5 mL) were added cyclopentyl isonitrile (250 mg, 291 μL, 2.6 mmol) followed by perchloric acid (26.1 mg, 23.3 μL, 260 μmol) at RT under nitrogen atmosphere. The resulting dark brown solution was stirred for 15 h at RT by which time LC/MS analysis indicated the presence of the desired peak. There are no solids formed after dilution with diethyl ether. Then, the solvent was removed under vacuum. The brown solid residue was dissolved in minimum methanol and then it was diluted with diethyl ether. The resulting solution was stored in the refrigerator for 15 h, but there were no solids formed. Then, the solvent was removed under vacuum and the brown residue was purified using an ISCO (80 g) column chromatography eluting with 0-50% ethyl acetate in hexanes. The desired fractions were combined and the solvent was removed under vacuum to obtain 416 mg (43% yield) of 3-(cyclopentylamino)-2-(3-methoxynaphthalen-2-yl)-1H-imidazo[1,2-b]pyrazole-7-carbonitrile as an off-white solid. LC/MS calcd. for $C_{22}H_{21}N_5O$ (m/e) 371.44, obsd. 372.0 (M+H, ES+).

Step 2: Preparation of (E)-5-amino-1-(1-(cyclopentylimino)-2-(3-methoxynaphthalen-2-yl)-2-oxoethyl)-1H-pyrazole-4-carbonitrile A light yellow solution of 3-(cyclopentylamino)-2-(3-methoxynaphthalen-2-yl)-1H-imidazo[1,2-b]pyrazole-7-carbonitrile (150 mg, 0.404 mmol) in DMSO (6 mL) was stored for 40 days at RT. Then, it was poured into a mixture of water and brine solution (~150 mL) and the organic compound was extracted into ethyl acetate (2×50 mL). The combined extracts were washed with brine solution and dried over anhydrous $MgSO_4$. Filtration and concentration gave the light yellow oil which was purified using an ISCO (40 g) column chromatography eluting with 0-60% ethyl acetate in hexanes. The desired fractions were combined and the solvent was removed under vacuum to isolate 36 mg (23% yield) of (E)-5-amino-1-(1-(cyclopentylimino)-2-(3-methoxynaphthalen-2-yl)-2-oxoethyl)-1H-pyrazole-4-carbonitrile as a light yellow solid. $^1$H NMR (400 MHz, DMSO-$d_6$) δ: 1.42-1.64 (br m, 4H), 1.64-1.80 (br, 4H), 3.75 (p, 1H), 3.77 (s, 3H), 7.45 (t, J=2.4 Hz, 1H), 7.48 (s, 1H), 7.64 (s, 1H), 7.65 (t, J=2.4 Hz, 1H) 7.88 (d, 1H), 8.10 (br s, 2H), 8.12 (d, 1H), 8.62 (s, 1H). LC/MS calcd. for $C_{22}H_{21}N_5O_2$ (m/e) 387.441, obsd. 388.0 (M+H, ES+).

Example 8

(E)-5-Amino-1-(1-(cyclopentylimino)-2-(6-methoxy-2,3-dihydro-1H-inden-5-yl)-2-oxoethyl)-1H-pyrazole-4-carbonitrile

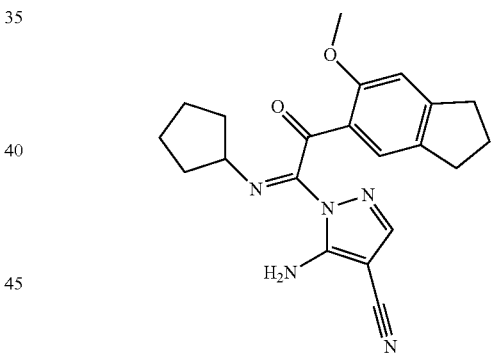

Step 1: Preparation of 3-(cyclopentylamino)-2-(6-methoxy-2,3-dihydro-1H-inden-5-yl)-1H-imidazo[1,2-b]pyrazole-7-carbonitrile To a mixture of 5-amino-1H-pyrazole-4-carbonitrile (193 mg, 1.79 mmol) and 6-methoxy-2,3-dihydro-1H-indene-5-carbaldehyde (315 mg, 1.79 mmol) in a vial under nitrogen atmosphere were added methanol (10 mL) followed by cyclopentyl isonitrile (172 mg, 200 μL, 1.79 mmol) and perchloric acid (35.9 mg, 32.1 μL, 0.358 mmol) at RT. Then, the resulting light yellow suspension was stirred for 15 h and the resulting solids were collected by filtration and washed with methanol. After air drying, 55 mg (8.5% yield) of 3-(cyclopentylamino)-2-(6-methoxy-2,3-dihydro-1H-inden-5-yl)-1H-imidazo[1,2-b]pyrazole-7-carbonitrile was isolated as an off-white solid. LC/MS calcd. for $C_{21}H_{23}N_5O$ (m/e) 361.44, obsd. 362.1 (M+H, ES+).

Step 2: Preparation of (E)-5-amino-1-(1-(cyclopentylimino)-2-(6-methoxy-2,3-dihydro-1H-inden-5-yl)-2-oxoethyl)-1H-pyrazole-4-carbonitrile A light yellow solution of 3-(cyclopentylamino)-2-(6-methoxy-2,3-dihydro-1H-inden-5-yl)-1H-imidazo[1,2-b]pyrazole-7-carbonitrile (55 mg, 0.152 mmol) in DMSO (20 mL) was stored at RT for several days. It became a brown solution within a day. After 53 days, the dark brown solution was poured into water (500 mL) and then the organic compound was extracted into ethyl acetate (2×100 mL). The combined extracts were washed with water, brine solution and dried and concentrated to obtain ~70 mg of the dark brown residue which was purified using an ISCO (40 g) column chromatography eluting with 0-50% ethyl acetate in hexanes. The desired fractions were combined and the solvent was removed under vacuum to obtain 12 mg (21% yield) of (E)-5-amino-1-(1-(cyclopentylimino)-2-(6-methoxy-2,3-dihydro-1H-inden-5-yl)-2-oxoethyl)-1H-pyrazole-4-carbonitrile as a light yellow solid. $^1$H NMR (400 MHz, DMSO-$d_6$) δ: 1.03-1.62 (br m, 4H), 1.62-1.82 (br m, 4H), 2.05 (p, 2H), 2.87 (t, 2H), 2.93 (t, 2H), 3.63 (s, 3H), 3.67 (br m, 1H), 7.05 (s, 1H), 7.63 (s, 1H), 7.73 (s, 1H), 8.06 (br s, 2H). LC/MS calcd. for $C_{21}H_{23}N_5O_2$ (m/e) 377.44, obsd. 378.1 (M+H, ES+).

Example 9

(E)-5-Amino-1-(1-(cyclohexylimino)-2-(2,4-dimethoxyphenyl)-2-oxoethyl)-1H-pyrazole-4-carbonitrile

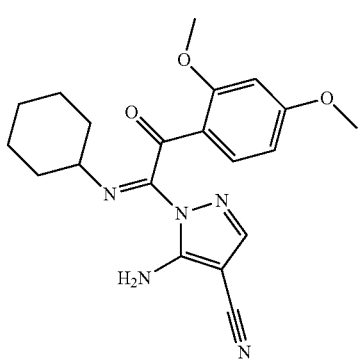 [SMILES: COc1ccc(C(=O)/C(=N\C2CCCCC2)n2ncc(C#N)c2N)c(OC)c1]

Step 1: Preparation of 3-(cyclohexylamino)-2-(2,4-dimethoxyphenyl)-1H-imidazo[1,2-b]pyrazole-7-carbonitrile To a mixture of 5-amino-1H-pyrazole-4-carbonitrile (491 mg, 4.54 mmol) and 2,4-dimethoxybenzaldehyde (754 mg, 4.54 mmol) in a vial under nitrogen atmosphere were added methanol (20 mL) followed by cyclohexyl isonitrile (500 mg, 581 μL, 4.54 mmol) and perchloric acid (91.2 mg, 81.4 μL, 0.908 mmol) at RT. Then, the resulting brown solution was stirred for 15 h by which time lots of solid was formed. These solids were collected by filtration and washed with methanol. After air drying, 495 mg (30% yield) of 3-(cyclohexylamino)-2-(2,4-dimethoxyphenyl)-1H-imidazo[1,2-b]pyrazole-7-carbonitrile was isolated as a white solid. LC/MS calcd. for $C_{20}H_{23}N_5O_2$ (m/e) 365.43, obsd. 366.0 (M+H, ES+).

Step 2: Preparation of (E)-5-amino-1-(1-(cyclohexylimino)-2-(2,4-dimethoxyphenyl)-2-oxoethyl)-1H-pyrazole-4-carbonitrile A light yellow solution of 3-(cyclohexylamino)-2-(2,4-dimethoxyphenyl)-1H-imidazo[1,2-b]pyrazole-7-carbonitrile (470 mg, 1.29 mmol) in DMSO (100 mL) was stored at RT for several days. It became a brown solution within a day and LC/MS analysis of the mixture was checked after 30 days. After 53 days, the dark brown solution was poured into water (500 mL) and then the organic compound was extracted into ethyl acetate (2×100 mL). The combined extracts were washed with water, brine solution and dried and concentrated to obtain ~250 mg of the dark brown residue which was purified using an ISCO (40 g) column chromatography eluting with 0-50% ethyl acetate in hexanes. The desired fractions were combined and the solvent was removed under vacuum to obtain 105 mg (21% yield) of (E)-5-amino-1-(1-(cyclohexylimino)-2-(2,4-dimethoxyphenyl)-2-oxoethyl)-1H-pyrazole-4-carbonitrile as an off-white solid. $^1$H NMR (400 MHz, DMSO-$d_6$) δ: 1.00-1.75 (br m, 10H), 3.20 (m, 1H), 3.66 (s, 3H), 3.88 (s, 3H), 6.62 (d, 1H), 6.72 (dd, 1H), 7.63 (s, 1H), 7.87 (d, 1H), 8.10 (br s, 2H). LC/MS calcd. for $C_{19}H_{21}N_5O_3$ (m/e) 381.434, obsd. 382.1 (M+H, ES+).

Example 10

(E)-5-Amino-1-(2-(2,4-dimethoxyphenyl)-1-(iso-propylimino)-2-oxoethyl)-1H-pyrazole-4-carbonitrile

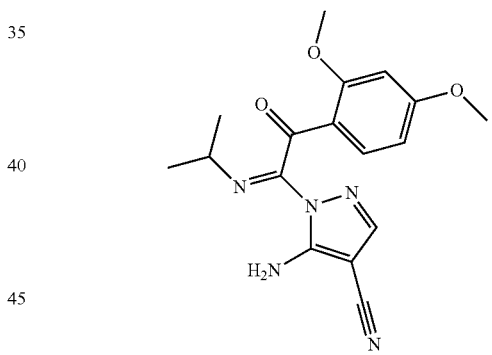

Step 1: Preparation of 2-(2,4-dimethoxyphenyl)-3-(iso-propylamino)-1H-imidazo[1,2-b]pyrazole-7-carbonitrile To a mixture of 5-amino-1H-pyrazole-4-carbonitrile (771 mg, 7.13 mmol) and 2,4-dimethoxybenzaldehyde (1.19 g, 7.13 mmol) in a vial under nitrogen atmosphere were added methanol (20 mL) followed by iso-propyl isonitrile (500 mg, 581 μL, 7.13 mmol) and perchloric acid (143 mg, 128 μL, 1.43 mmol) at RT. Then, the resulting brown solution was stirred for 15 h by which time LC/MS analysis indicated the presence of the desired product. Then, the solvent was removed under vacuum and the residue was purified using an ISCO (80 g) column chromatography eluting with 0-50% ethyl acetate in hexanes. The desired fractions were combined and the solvent was removed under vacuum to obtain 647 mg (28% yield) of 2-(2,4-dimethoxyphenyl)-3-(iso-propylamino)-1H-imidazo[1,2-b]pyrazole-7-carbonitrile as a light yellow solid. LC/MS calcd. for $C_{17}H_{19}N_5O_2$ (m/e) 325.37, obsd. 326.0 (M+H, ES+).

Step 2: Preparation of (E)-5-amino-1-(2-(2,4-dimethoxyphenyl)-1-(iso-propylimino)-2-oxoethyl)-1H-pyrazole-4-carbonitrile A light yellow solution of 2-(2,4-dimethoxyphenyl)-3-(iso-propylamino)-1H-imidazo[1,2-b]pyrazole-7-carbonitrile (500 mg, 1.54 mmol) in DMSO (100 mL) was stored for several days at RT. Within a day, it became a brown solution and after 55 days LC/MS analysis was checked. After 55 days, the dark brown solution was poured into water (500 mL) and then the organic compound was extracted into ethyl acetate (2×100 mL). The combined extracts were washed with water, brine solution and dried and concentrated to obtain 298 mg of the dark brown residue which was purified using an ISCO (80 g) column chromatography eluting with 0-50% ethyl acetate in hexanes. The pure fractions were combined and the solvent was removed under vacuum to obtain 65 mg (12% yield) of (E)-5-amino-1-(2-(2,4-dimethoxyphenyl)-1-(iso-propylimino)-2-oxoethyl)-1H-pyrazole-4-carbonitrile as a light yellow solid. $^1$H NMR (400 MHz, DMSO-$d_6$) δ: 1.09 (br, 6H), 3.49 (br m, 1H), 3.66 (s, 3H), 3.87 (s, 3H), 6.66 (s, 1H), 6.75 (d, 1H), 7.67 (s, 1H), 7.89 (d, 1H), 8.12 (br s, 2H). LC/MS calcd. for $C_{17}H_{19}N_5O_3$ (m/e) 341.36, obsd. 342.0 (M+H, ES+).

Example 11

(E)-5-Amino-1-(2-(4-benzyloxy-2-methoxyphenyl)-1-(cyclopentylimino)-2-oxoethyl)-1H-pyrazole-4-carbonitrile

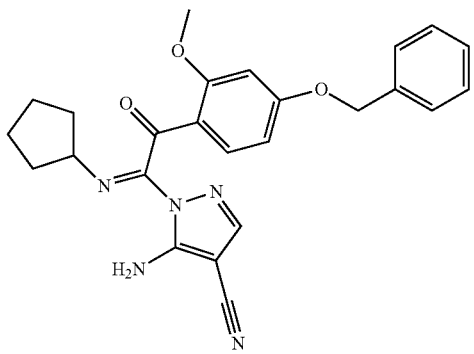 [SMILES: COc1cc(OCc2ccccc2)ccc1C(=O)/C(=N\C1CCCC1)n1ncc(C#N)c1N]

Step 1: Preparation of 2-(4-benzyloxy-2-methoxyphenyl)-3-(cyclopentylamino)-1H-imidazo[1,2-b]pyrazole-7-carbonitrile To a mixture of 5-amino-1H-pyrazole-4-carbonitrile (193 mg, 1.79 mmol) and 4-(benzyloxy)-2-methoxybenzaldehyde (433 mg, 1.79 mmol) in a vial under nitrogen atmosphere were added methanol (10 mL) followed by cyclopentyl isonitrile (172 mg, 200 μL, 1.79 mmol) and perchloric acid (35.9 mg, 32.1 μL, 0.358 mmol) at RT. Then, the resulting brown solution was stirred for 15 h by which time lot of solids precipitated. These solids were collected by filtration and washed with methanol. After air drying, 320 mg of (42%) 2-(4-benzyloxy-2-methoxyphenyl)-3-(cyclopentylamino)-1H-imidazo[1,2-b]pyrazole-7-carbonitrile, the desired product was isolated as a white solid. LC/MS calcd. for $C_{25}H_{25}N_5O_2$ (m/e) 427.5, obsd. 428.1 (M+H, ES+).

Step 2: Preparation of (E)-5-Amino-1-(2-(4-benzyloxy-2-methoxyphenyl)-1-(cyclopentylimino)-2-oxoethyl)-1H-pyrazole-4-carbonitrile A light yellow solution of 2-(4-(benzyloxy)-2-methoxyphenyl)-3-(cyclopentylamino)-1H-imidazo[1,2-b]pyrazole-7-carbonitrile (298 mg, 0.697 mmol) in DMSO (80 mL) was stored at RT for several days. It became a brown solution within a day and LCMS analysis of the mixture was checked after 30 days. After 53 days, the dark brown solution was poured into water (500 mL) and then the organic compound was extracted into EA (2×100 mL). The combined extracts were washed with water and brine solution and dried and concentrated to obtain ~450 mg of the dark brown residue which was purified using an ISCO (80 g) column chromatography eluting with 0-50% EA in hexanes. The desired fractions were combined and the solvent was removed under vacuum to obtain 85 mg (27.5%) of (E)-5-amino-1-(2-(4-benzyloxy-2-methoxyphenyl)-1-(cyclopentylimino)-2-oxoethyl)-1H-pyrazole-4-carbonitrile as a light yellow solid. $^1$H NMR (400 MHz, DMSO-$d_6$) δ: 1.45-1.53 (br m, 4H), 1.53-1.85 (br m, 4H), 3.65 (brs, 4H), 5.27 (s, 2H), 6.74 (d, J=2.4 Hz, 1H), 6.81 (dd, J=8.2 Hz, 2.3 Hz, 1H), 7.35-7.5 (m, 5H), 7.61 (s, 1H), 7.86 (d, J=8.5 Hz, 1H), 8.06 (br s, 2H). LC/MS calcd. for $C_{25}H_{25}N_5O_3$ (m/e) 443.5, obsd. 444.1 (M+H, ES+).

Example 12

(E)-5-Amino-1-(1-(cyclopentylimino)-2-(3,4,5-trimethoxyphenyl)-2-oxoethyl)-1H-pyrazole-4-carbonitrile

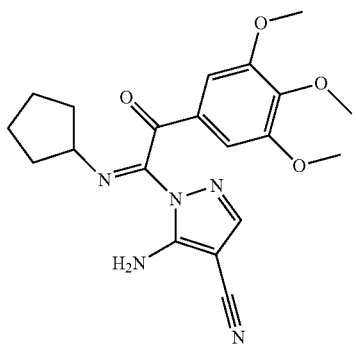 [SMILES: COc1cc(C(=O)/C(=N\C2CCCC2)n2ncc(C#N)c2N)cc(OC)c1OC]

Step 1: Preparation of 3-(cyclopentylamino)-2-(3,4,5-trimethoxyphenyl)-1H-imidazo[1,2-b]-pyrazole-7-carbonitrile To a clear light brown solution of 3,4,5-trimethoxybenzaldehyde (600 mg, 3.06 mmol) and 5-amino-1H-pyrazole-4-carbonitrile (331 mg, 3.06 mmol) in methanol (10 mL) in a 20 mL vial were added cyclopentyl isonitrile (294 mg, 342 μL, 3.06 mmol) and perchloric acid (61.4 mg, 54.9 μL, 0.612 mmol) at RT under nitrogen atmosphere. Then, the nitrogen line was disconnected and the resulting brown suspension was stirred for 15 h at RT. The off-white solids were collected by filtration and washed with methanol. After drying in the air, 375 mg (32%) of 3-(cyclopentylamino)-2-(3,4,5-trimethoxyphenyl)-1H-imidazo[1,2-b]pyrazole-7-carbonitrile was isolated as an off-white solid. LC/MS calcd. for $C_{20}H_{23}N_5O_3$ (m/e) 381.434, obsd. 382.0 (M+H, ES+).

Step 2: Preparation of (E)-5-amino-1-(1-(cyclopentylimino)-2-(3,4,5-trimethoxyphenyl)-2-oxoethyl)-1H-pyrazole-4-carbonitrile A light brown solution of 3-(cyclopentylamino)-2-(3,4,5-trimethoxyphenyl)-1H-imidazo[1,2-b]pyrazole-7-carbonitrile (330 mg, 0.865 mmol) in DMSO (100 mL) was stored for 60 days at RT. Within one day, it became a light brown solution and no precipitation was observed during these 60 days. Then, it was poured into water (1 L) and the resulting precipitate was extracted into EA (2×75 mL). The combined extracts were washed with water, brine solution, and dried over anhydrous $MgSO_4$. Filtration and concentration gave the crude solid which was purified using an ISCO (40 g) column chromatography eluting with 0-70% EA in hexanes. The desired fractions were combined and the solvent was removed under vacuum to obtain 115 mg (33.4%) of (E)-5-amino-1-(1-(cyclopentylimino)-2-(3,4,5-trimethoxyphenyl)-2-oxoethyl)-1H-pyrazole-4-carbonitrile as a light yellow solid. $^1$H NMR (400 MHz, DMSO-$d_6$): 1.50-1.80 (br m, 8H), 3.67 (p, 1H), 3.79 (s, 3H), 3.81 (s, 6H), 7.06 (s, 2H), 7.7 (s, 1H), 8.12 (br s, 2H). LC/MS calcd. for $C_{20}H_{23}N_5O_4$ (m/e) 397.433, obsd. 398.3 (M+H, ES+).

Example 13

Calcium Flux Assay Using Fluorometric Imaging Plate Reader (FLIPR)

Cell Culture Conditions: The ChemiScreen Calcium-optimized stable cell line containing the human recombinant LPA1 Lysophospholipid receptor was purchased from Chemicon International, Inc./Millipore. The cells were cultured in DMEM-high glucose supplemented with 10% fetal bovine serum, 2 mM glutamine, 100 U/mL penicillin/100 µg/mL streptomycin, 1× non-essential amino acids, 10 mM HEPES and 0.25 mg/mL Geneticin. Cells were harvested with trypsin-EDTA and counted using ViaCount reagent. The cell suspension volume was adjusted to $2.0 \times 10^5$ cells/mL with complete growth media. Aliquots of 50 µL were dispensed into 384 well black/clear tissue culture treated plates (BD) and the microplates were placed in a 37° C. incubator overnight. The following day plates were used in the assay.

Dye Loading and Assay: Loading Buffer (FLIPR Calcium-4, Molecular Devices) was prepared by dissolving the contents of one bottle into 100 mL Hank's Balanced Salt Solution containing 20 mM HEPES and 2.5 mM probenecid. Plates were loaded onto Biotek plate washer and growth media was removed and replaced with 20 µL of Hank's Balanced Salt Solution containing 20 mM HEPES and 2.5 mM probenecid, followed by 25 µL of Loading Buffer. The plates were then incubated for 30 minutes at 37° C.

During the incubation, test compounds were prepared by adding 90 µL of HBSS/20 mM HEPES/0.1% BSA buffer to 2 µL of serially diluted compounds. To prepare serial dilutions, 10 mM stocks of compounds were prepared in 100% DMSO. The compound dilution plate was set up as follows: well #1 received 29 µL of stock compound and 31 µL DMSO; wells 2-10 received 40 µL of DMSO; mixed and transferred 20 µL of solution from well #1 into well #2; continued with 1:3 serial dilutions out 10 steps; transferred 2 µL of diluted compound into duplicate wells of 384 well "assay plate" and then added the 90 µL of buffer.

After incubation, both the cell and "assay" plates were brought to the FLIPR and 20 µL of the diluted compounds were transferred to the cell plates by the FLIPR. Compound addition was monitored by FLIPR to detect any agonist activity of the compounds. Plates were then incubated for 30 minutes at RT protected from light. After the incubation, plates were returned to the FLIPR and 20 µL of 4.5× concentrated agonist was added to the cell plates. During the assay, fluorescence readings were taken simultaneously from all 384 wells of the cell plate every 1.5 seconds. Five readings were taken to establish a stable baseline, then 20 µL of sample was rapidly (30 µL/sec) and simultaneously added to each well of the cell plate. The fluorescence was continuously monitored before, during and after sample addition for a total elapsed time of 100 seconds. Responses (increase in peak fluorescence) in each well following agonist addition was determined. The initial fluorescence reading from each well, prior to ligand stimulation, was used as zero baseline value for the data from that well. The responses were expressed as % inhibition of the buffer control. The $IC_{50}$ value, defined as the concentration of a compound required for 50% inhibition of the buffer control, was calculated by fitting the percent inhibition data for 10 concentrations to a sigmoidal dose-response (4 parameter logistic) model using Genedata Condoseo program [model 205, $F(x)=(A+(B-A)/(1+((C/x)^D)))$] and the results shown in Table 1 below:

TABLE 1

| LPA1 and LPA3 antagonist activities | | |
|---|---|---|
| Example# | LPA1 $IC_{50}$ (µM) and/or inhibition % @ µM | LPA3 inhibition % @ µM |
| 1 | 0.0798 (98% @ 30) | 22% @ 30 |
| 2 | 0.586 (100% @ 30) | 13% @ 30 |
| 3 | 2.94 (96% @ 30) | <1% @ 30 |
| 4 | 49% @ 30 | 3% @ 30 |
| 5 | 0.074 (99.8% @ 30) | <5% @ 30 |
| 6 | 3.36 (79.2% @ 10) | 7.5% @ 30 |
| 7 | 0.806 (77.5% @ 30) | 2% @ 30 |
| 8 | 0.825 (78.4% @ 30) | 19.1% @ 30 |
| 9 | 0.510 (84.9% @ 30) | 29% @ 30 |
| 10 | 0.111 (88.2% @ 30) | 21% @ 30 |
| 11 | 48% @ 30 | 23% @ 30 |
| 12 | 13% @ 5 | 14% @ 30 |

It is to be understood that the invention is not limited to the particular embodiments of the invention described above, as variations of the particular embodiments may be made and still fall within the scope of the appended claims.

The invention claimed is:
1. A compound of formula (I):

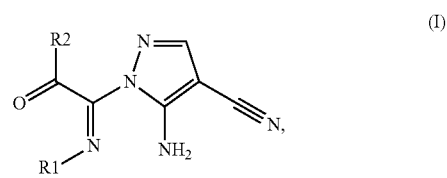

wherein:
R1 is lower alkyl or cycloalkyl; and
R2 is phenyl, unsubstituted or mono-, bi- or tri-substituted independently with alkoxy, phenyl alkoxy, lower alkyl or halogen; naphthalenyl, unsubstituted or substituted with alkoxy; or indenyl, unsubstituted or substituted with alkoxy;
or a pharmaceutically acceptable salt thereof.

2. The compound according to claim 1, wherein R1 is methyl, propyl, iso-propyl or tert-butyl.

3. The compound according to claim 1, wherein R1 is cyclopentyl or cyclohexyl.

4. The compound according to claim 1, wherein R2 is unsubstituted phenyl.

5. The compound according to claim 1, wherein R2 is phenyl mono-substituted with ethyl, bromo, fluoro or methoxy.

6. The compound according to claim 1, wherein R2 is phenyl di-substituted independently with methoxy, benzyloxy or fluoro.

7. The compound according to claim 1, wherein R2 is phenyl tri-substituted with methoxy.

8. The compound according to claim 1, wherein R2 is naphthalenyl substituted with methoxy.

9. The compound according to claim 1, wherein R2 is indenyl substituted with methoxy.

10. The compound according to claim 1, wherein said compound is:
 (E)-5-Amino-1-(1-(cyclopentylimino)-2-(2,4-dimethoxyphenyl)-2-oxoethyl)-1H-pyrazole-4-carbonitrile;
 (E)-5-Amino-1-(1-(cyclopentylimino)-2-(4-ethylphenyl)-2-oxoethyl)-1H-pyrazole-4-carbonitrile;
 (E)-5-Amino-1-(1-(cyclopentylimino)-2-(4-bromophenyl)-2-oxoethyl)-1H-pyrazole-4-carbonitrile;
 (E)-5-Amino-1-(1-(cyclopentylimino)-2-(4-fluoro-2-methoxyphenyl)-2-oxoethyl)-1H-pyrazole-4-carbonitrile;
 (E)-5-Amino-1-(1-(cyclopentylimino)-2-(2-fluoro-4-methoxyphenyl)-2-oxoethyl)-1H-pyrazole-4-carbonitrile;
 (E)-5-Amino-1-(1-(cyclopentylimino)-2-(2,4,5-trimethoxyphenyl)-2-oxoethyl)-1H-pyrazole-4-carbonitrile;
 (E)-5-Amino-1-(1-(cyclopentylimino)-2-(3-methoxynaphthalen-2-yl)-2-oxoethyl)-1H-pyrazole-4-carbonitrile;
 (E)-5-Amino-1-(1-(cyclopentylimino)-2-(6-methoxy-2,3-dihydro-1H-inden-5-yl)-2-oxoethyl)-1H-pyrazole-4-carbonitrile;
 (E)-5-Amino-1-(1-(cyclohexylimino)-2-(2,4-dimethoxyphenyl)-2-oxoethyl)-1H-pyrazole-4-carbonitrile;
 (E)-5-Amino-1-(2-(2,4-dimethoxyphenyl)-1-(iso-propylimino)-2-oxoethyl)-1H-pyrazole-4-carbonitrile;
 (E)-5-Amino-1-(2-(4-benzyloxy-2-methoxyphenyl)-1-(cyclopentylimino)-2-oxoethyl)-1H-pyrazole-4-carbonitrile; or
 (E)-5-Amino-1-(1-(cyclopentylimino)-2-(3,4,5-trimethoxyphenyl)-2-oxoethyl)-1H-pyrazole-4-carbonitrile.

11. A pharmaceutical composition, comprising a therapeutically effective amount of a compound according to claim 1 and a therapeutically inert carrier.

12. A method for the treatment of pulmonary fibrosis, which method comprises the step of administering a therapeutically effective amount of a compound according to claim 1 to a patient in need thereof.

* * * * *